United States Patent [19]

Shimura

[11] Patent Number: 5,418,373

[45] Date of Patent: May 23, 1995

[54] METHOD FOR FORMING RADIATION IMAGES

[75] Inventor: Kazuo Shimura, Kanagawa, Japan

[73] Assignee: Fuji Photo Film Co., Ltd., Kanagawa, Japan

[21] Appl. No.: 117,621

[22] Filed: Sep. 8, 1993

[30] Foreign Application Priority Data

Sep. 8, 1992 [JP] Japan .................................. 4-239411

[51] Int. Cl.$^6$ ............................................ G03B 42/02
[52] U.S. Cl. ...................................... 250/583; 378/62; 378/207
[58] Field of Search ................... 250/583; 378/53, 56, 378/98.9, 98.11, 99, 207, 62, 111

[56] References Cited

U.S. PATENT DOCUMENTS

| | | | |
|---|---|---|---|
| 3,996,471 | 12/1976 | Fletcher et al. | 378/53 |
| 4,761,739 | 8/1988 | Shimura | 250/583 X |
| 5,187,731 | 2/1993 | Shimura | 378/207 |
| 5,210,415 | 5/1993 | Ito | 378/98.11 |

FOREIGN PATENT DOCUMENTS

2412161 9/1974 Germany .................... 378/53

*Primary Examiner*—Constantine Hannaher
*Assistant Examiner*—Edward J. Glick
*Attorney, Agent, or Firm*—Sughrue, Mion, Zinn, Macpeak & Seas

[57] ABSTRACT

A tube voltage, at which each of at least two kinds of radiation having different energy levels is produced, is adjusted such that a ratio between a change in the image density of bones, which change occurs due to a beam hardening phenomenon of the radiation having a high energy level, and a change in the image density of the bones, which change occurs due to a beam hardening phenomenon of the radiation having a low energy level, may become approximately equal to a ratio between subtraction factors employed in a subtraction process. Each of at least two kinds of the radiation, each of which has been produced at the thus adjusted tube voltage, is irradiated to one of at least two stimulable phosphor sheets, and radiation images of the object are thereby stored on the stimulable phosphor sheets. The radiation images are then photoelectrically read out, and digital image signals are thereby obtained. Image signal components of the digital image signals, which represent corresponding picture elements in the radiation images, are then subtracted from each other, and a difference signal is thereby obtained which represents the image of only the bones represented by the radiation images.

16 Claims, 5 Drawing Sheets log Sa log Sb log $S_A$ log $S_B$

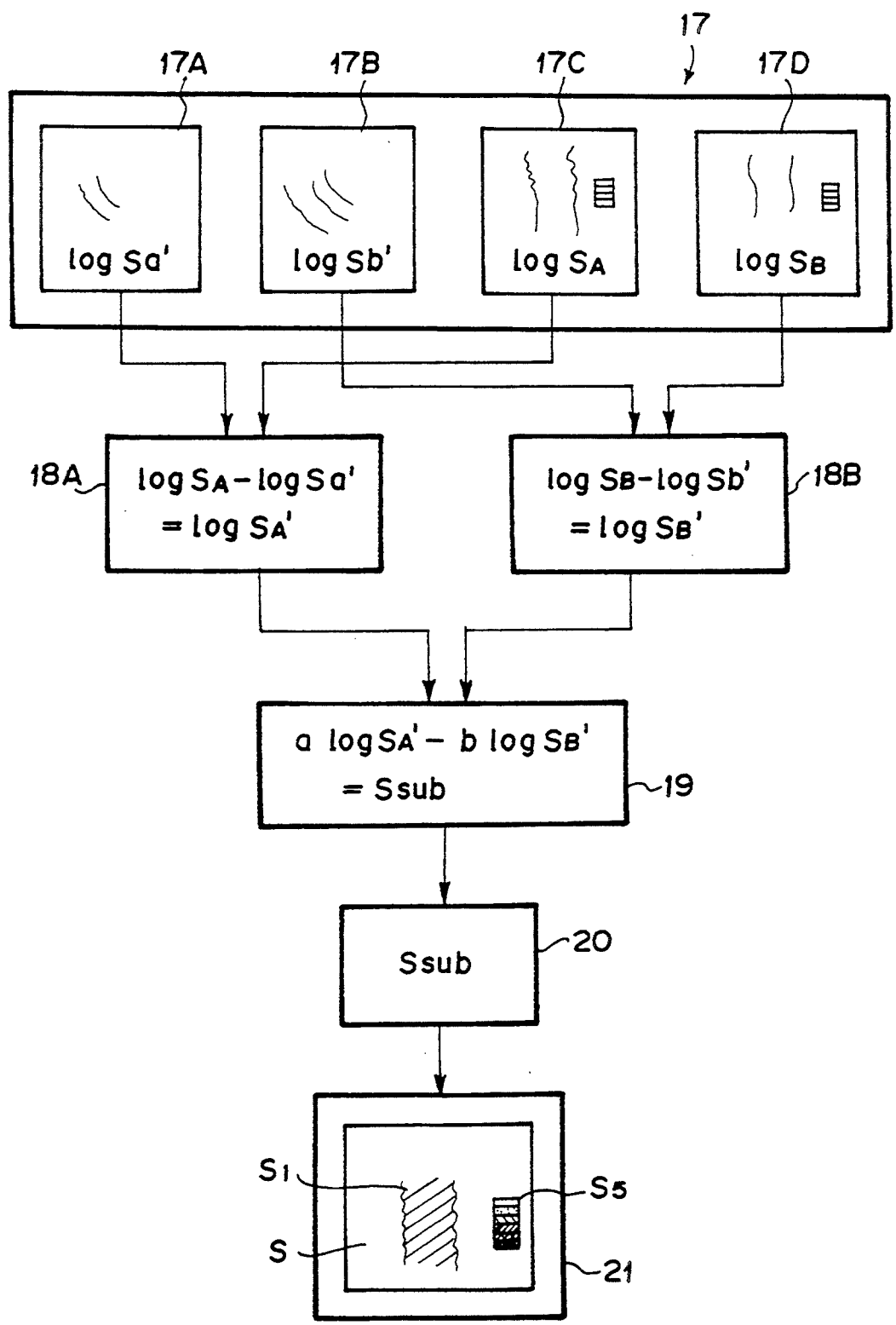

METHOD FOR FORMING RADIATION IMAGES

BACKGROUND OF THE INVENTION

1. Field of the Invention

This invention relates to a method for forming a radiation image and a method for quantitatively analyzing bone calcium, wherein the method for forming a radiation image is used. This invention particularly relates to a method for forming a radiation image by using stimulable phosphor sheets and an energy subtraction processing technique.

2. Description of the Prior Art

When certain kinds of phosphors are exposed to radiation such as X-rays, α-rays, β-rays, γ-rays, cathode rays or ultraviolet rays, they store part of the energy of the radiation. Then, when the phosphor which has been exposed to the radiation is exposed to stimulating rays, such as visible light, light is emitted by the phosphor in proportion to the amount of energy stored thereon during its exposure to the radiation. A phosphor exhibiting such properties is referred to as a stimulable phosphor.

As disclosed in U.S. Pat. Nos. 4,258,264, 4,276,473, 4,315,318, 4,387,428, and Japanese Unexamined Patent Publication No. 56(1981)-11395, it has been proposed to use stimulable phosphors in radiation image recording and reproducing systems. Specifically, a radiation image of an object, such as a human body, is recorded on a sheet provided with a layer of the stimulable phosphor (hereinafter referred to as a stimulable phosphor sheet). The stimulable phosphor sheet, on which the radiation image has been stored, is then scanned with stimulating rays, such as a laser beam, which cause it to emit light in proportion to the amount of energy stored thereon during its exposure to the radiation. The light emitted by the stimulable phosphor sheet, when it is exposed to the stimulating rays, is photoelectrically detected and converted into an electric image signal. The electric image signal is then processed, and the processed image signal is then used during the reproduction of a visible image which has good image quality and can serve as an effective tool in, particularly, the efficient and accurate diagnosis of an illness. The visible image finally obtained may be reproduced in the form of a hard copy or may be displayed on a display device, such as a cathode ray tube (CRT) display device. In the radiation image recording and reproducing systems, the stimulable phosphor sheet is used to store the radiation image temporarily so that a final visible image can be reproduced therefrom on a final recording medium. For the sake of economy, therefore, it is desirable that the stimulable phosphor sheet be used repeatedly.

In order that the stimulable phosphor sheets may be reused as described above, the energy remaining on the stimulable phosphor sheet after it has been scanned with stimulating rays should be erased. For this purpose, the stimulable phosphor sheet may be exposed to light or heat as described in, for example, U.S. Pat. No. 4,400,619 or Japanese Unexamined Patent Publication No. 56(1981)-12599. The stimulable phosphor sheet may then be used again for the recording of a radiation image.

Also, techniques for carrying out subtraction processing on radiation images have heretofore been known. When subtraction processing is to be carried out, at least two radiation images recorded under different conditions are photoelectrically read out, and digital image signals which represent the radiation images are obtained. The image signal components of the digital image signals which represent corresponding picture elements in the radiation images are then subtracted from each other, and a difference signal is thereby obtained which represents the image of a specific structure or part of the object represented by the radiation images. With the subtraction processing method, at least two digital image signals are subtracted from each other in order to obtain a difference signal, and the radiation image of a specific structure can be reproduced from the difference signal.

Basically, subtraction processing is carried out with either the so-called temporal (time difference) subtraction processing method or the so-called energy subtraction processing method. In the former method, in order for the image of a specific structure of an object to be extracted from the image of the whole object, the image signal representing a radiation image obtained without injection of contrast media is subtracted from the image signal representing a radiation image in which the image of the specific structure of the object is enhanced by the injection of contrast media. In the latter method, an object is exposed several times to radiation with different energy distributions, or the energy distribution of the radiation, which has passed through an object, is changed after it has been irradiated onto one of at least two radiation storage means, after which the radiation impinges upon the second storage means. In this manner, at least two radiation images, in which different images of a specific structure are embedded, are obtained. Thereafter, the image signals representing at least two radiation images are weighted appropriately, when necessary, and subjected to a subtraction process in order to extract the image of the specific structure. In general, of the energy subtraction processing method, the method, wherein an object is exposed several times to radiation with different energy distributions, is referred to as the "two-shot energy subtraction processing method." Also, the method, wherein the energy distribution of the radiation, which has passed through an object, is changed after it has been irradiated onto one of at least two radiation storage means, after which the radiation impinges upon the second storage means, is referred to as the "one-shot energy subtraction processing method."

It is advantageous that stimulable phosphor sheets are utilized during energy subtraction processing wherein a subtraction process is carried out on image signals. For example, in the two-shot energy subtraction processing method, a first stimulable phosphor sheet located at the position for image recording is quickly exchanged with a second stimulable phosphor sheet and, at the same time, the level of the tube voltage of an X-ray tube is quickly changed over such that radiation having a high energy level and radiation having a low energy level may be sequentially irradiated to an object. In this manner, a radiation image is recorded on one of the stimulable phosphor sheets with the radiation having a high energy level, and a radiation image is recorded on the other stimulable phosphor sheet with the radiation having a low energy level. In the one-shot energy subtraction processing method, for example, at least two stimulable phosphor sheets are placed one upon another with a radiation energy separating filter, such as a copper plate, intervening therebetween. Alternatively, at least two stimulable phosphor sheets having different radiation absorption characteristics are placed one upon another. In this manner, different kinds of radiation images are simultaneously recorded on the stimulable phosphor sheets placed one upon another. The applicant proposed novel energy subtraction processing methods using stimulable phosphor sheets in, for example, U.S. Pat. Nos. 4,855,598 and 4,896,037.

Subtraction processing is extremely effective, particularly for medical diagnosis, and research has continued to develop improved subtraction processing methods. For example, it has been proposed to quantitatively analyze bone calcium by utilizing the energy subtraction processing technique, wherein patterns of soft tissues of an object are erased, and an image representing only the bones of the object is formed. In the quantitative analysis of bone calcium, amounts of calcium in bones of a human body, or the like, are quantitatively determined. Quantitative determination of the amounts of calcium in bones is necessary for preventing fractures of bones. Specifically, by investigating small changes in the amounts of calcium contained in bones, osteoporosis can be found early, and fractures of the bones can be prevented.

In U.S. Pat. No. 5,122,664, the applicant proposed a novel method for quantitatively analyzing bone calcium, wherein energy subtraction processing is employed. Specifically, the applicant proposed a method for quantitatively analyzing bone calcium by carrying out energy subtraction processing wherein each of at least two stimulable phosphor sheets is exposed to one of at least two kinds of radiation, which have different energy distributions and have passed through an object constituted of bones and soft tissues, radiation images of the object are thereby recorded on the stimulable phosphor sheets, each of the stimulable phosphor sheets is thereafter exposed to stimulating rays, each radiation image is photoelectrically detected and converted into a digital image signal made up of a series of image signal components representing each radiation image, the image signal components of the digital image signals thus obtained, which image signal components represent corresponding picture elements in the radiation images, are then subtracted from each other, and a difference signal is thereby obtained which represents the image of only the bones represented by the radiation images. The proposed method for quantitatively analyzing bone calcium comprises the steps of:

i) recording a pattern of a bone calcium reference material, which simulates amounts of bone calcium varying step-wise, together with the pattern of the object when each of the radiation images of the object is recorded on each of the stimulable phosphor sheets, and ii) quantitatively analyzing bone calcium in the bones by comparing the image density of the patterns of the bones with the image density of the pattern of the bone calcium reference material, both patterns appearing in the image of only the bones (i.e., the bone image).

With the proposed method for quantitatively analyzing bone calcium, an image signal for compensation for the adverse effects of shading (such as nonuniformity in each stimulable phosphor sheet, nonuniformity in how radiation is irradiated to each stimulable phosphor sheet, and nonuniformity in how the light emitted by each stimulable phosphor sheet is detected) is obtained from the stimulable phosphor sheets exposed respectively to at least two kinds of radiation, which have different energy distributions and have not passed through the object. The image signal for compensation and the image signal representing the radiation image are then subtracted from each other. In this manner, adverse effects of the shading are eliminated such that an accurate analysis of bone calcium can be carried out.

However, in cases where an image is recorded with radiation having a broad energy distribution during energy subtraction processing, the so-called "beam hardening phenomenon" occurs. Specifically, the energy distribution of the radiation, which has passed through the object, shifts to the high energy side as a whole. If the beam hardening phenomenon occurs, the drawbacks will occur in that, for example, in a bone image in which soft tissue patterns have been erased, even if the bone structure is the same, the image density of the bone, which is located at a position at which the thickness of the object is large, becomes lower than the image density of the bone, which is located at a position at which the thickness of the object is small. Therefore, during the quantitative analysis of bone calcium, the problems will occur in that the results of determination of the bone density and the amount of bone calcium are adversely affected by the thickness of soft tissues overlapping upon the bone, and the accuracy of the determination cannot be kept high.

SUMMARY OF THE INVENTION

The primary object of the present invention is to provide a method for forming a radiation image, wherein adverse effects of a beam hardening phenomenon are reduced, and a radiation image is thereby obtained which accurately represents only the bone patterns without being adversely affected by the thickness of an object.

Another object of the present invention is to provide a method for quantitatively analyzing bone calcium, wherein the amount of bone calcium in bones is determined accurately by utilizing a radiation image which accurately represents only the bone patterns.

The present invention provides a method for forming a radiation image by carrying out energy subtraction processing wherein each of at least two stimulable phosphor sheets is exposed to one of at least two kinds of radiation, which have different energy levels and have passed through an object constituted of bones and soft tissues, radiation images of the object are thereby stored on the stimulable phosphor sheets, each of the stimulable phosphor sheets is thereafter exposed to stimulating rays, which cause the stimulable phosphor sheet to emit light in proportion to the amount of energy stored thereon during its exposure to the radiation, the emitted light is photoelectrically detected and converted into a digital image signal made up of a series of image signal components representing each of the radiation images, the image signal components of the digital image signals thus obtained, which image signal components represent corresponding picture elements in the radiation images, are then subtracted from each other, and a difference signal is thereby obtained which represents the image of only the bones represented by the radiation images, the method for forming a radiation image comprising the steps of:

i) adjusting a tube voltage, at which each of at least two kinds of the radiation having different energy levels is produced, such that a ratio between a change in the image density of the bones, which change occurs due to a beam hardening phenomenon of the radiation having a high energy level among at least two kinds of the radiation having different energy levels, and a change in the image density of the bones, which change occurs due to a beam hardening phenomenon of the radiation having a low energy level among at least two kinds of the radiation having different energy levels, may become approximately equal to a ratio between subtraction factors employed in the subtraction process, and ii) irradiating each of at least two kinds of the radiation, each of which has been produced at the thus adjusted tube voltage, to one of the stimulable phosphor sheets.

Specifically, with the method for forming a radiation image in accordance with the present invention, the tube voltage, at which each of at least two kinds of the radiation having different energy levels is produced, is adjusted in the manner described above. Each of at least two kinds of the radiation, each of which has been produced at the thus adjusted tube voltage, is irradiated to one of the stimulable phosphor sheets. In this manner, when the image signal components of the digital image signals, which image signal components represent corresponding picture elements in the radiation images to be subjected to energy subtraction processing, are subtracted from each other, a change in the image density of the bones, which change occurs due to the beam hardening phenomenon of the radiation having a high energy level, and a change in the image density of the bones, which change occurs due to the beam hardening phenomenon of the radiation having a low energy level, are canceled each other.

The present invention also provides a method for quantitatively analyzing bone calcium, wherein the method for forming a radiation image in accordance with the present invention is employed. The method for quantitatively analyzing bone calcium in accordance with the present invention is characterized by quantitatively analyzing bone calcium in the bones from the difference signal, which has been obtained with the method for forming a radiation image in accordance with the present invention.

With the method for forming a radiation image in accordance with the present invention, an image of only the bones can be obtained accurately.

Specifically, in cases where the tube voltage, at which each of at least two kinds of the radiation having different energy levels is produced, is adjusted in the manner described, changes in the image density of the bones are multiplied by the subtraction factors during the subtraction process, which is carried out in order to erase the patterns of the soft tissues. Therefore, complicated processes are not required, and the radiation image of only the bones can be obtained accurately.

Also, with the method for quantitatively analyzing bone calcium in accordance with the present invention, the pattern of the bone calcium reference material is stored together with the image pattern of the object. The bone calcium reference material is constituted of a plurality of sections, the radiation absorption amounts of which are known and vary step-wise. Therefore, the image density of the patterns of the bones of the object, on which the quantitative analysis of bone calcium is to be carried out, can be compared with several levels of image density of the step-like sections of the bone calcium reference material. Part of the step-like sections, the image density of which is closest to the image density of the patterns of the bones of the object, can thus be found. From the amount of bone calcium associated with the part of the step-like sections, which has thus been found, the amount of bone calcium in the bones can be determined.

A calibration curve, or the like, is prepared, which indicates the relationship between the image densities of the step-like sections of the phantom and the amounts of bone calcium. By referring to the calibration curve, the amount of bone calcium (a true value) in the bones can be found from the image density (a measured value) of the part of the step-like sections of the phantom.

Comparison of the image density may be carried out visually by displaying the image on a reproducing apparatus, such as a CRT display device. Alternatively, the comparison may be carried out by electrically rating the difference signal (i.e. the energy subtraction signal).

In the past, only the methods, wherein the radiation is converted into monochromatic radiation, were available in order to markedly reduce the adverse effects of the beam hardening phenomenon. For such purposes, a technique utilizing the diffraction phenomenon by a crystal or a technique using a K-edge filter must be used. With such conventional methods, burden to radiation tube cannot be kept light, and a complicated and expensive apparatus must be used. On the other hand, with the method for forming a radiation image in accordance with the present invention, marked reduction in the adverse effects of the beam hardening phenomenon can be achieved easily and at a low cost. As a result, an image of only the bones, in which the image density of the bones is expressed accurately, can be obtained. Also, with the method for quantitatively analyzing bone calcium in accordance with the present invention, the amount of bone calcium in the bones can be determined accurately by using the image, which has been formed with the method for forming a radiation image in accordance with the present invention.

BRIEF DESCRIPTION OF THE DRAWINGS

FIG. 7 is a block diagram showing how energy subtraction processing is carried out in the embodiment of the method for forming a radiation image in accordance with the present invention.

DESCRIPTION OF THE PREFERRED EMBODIMENTS

The present invention will hereinbelow be described in further detail with reference to the accompanying drawings.

Figure 1:
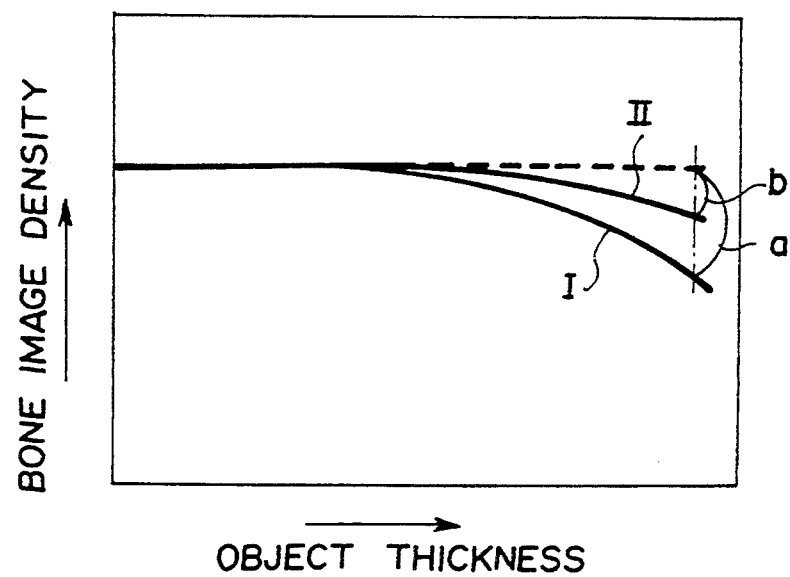
FIG. 1 is a graph showing the relationships between an object thickness and image density of bones in a radiation image, which has been recorded with radiation having a high energy level, and a radiation image, which has been recorded with radiation having a low energy level.

FIG. 1 is a graph showing the relationships between an object thickness and image density of bones in a radiation image, which has been recorded with radiation having a high energy level, and a radiation image, which has been recorded with radiation having a low energy level. In FIG. 1, "a" represents a change in the image density of bones due to a beam hardening phenomenon, which occurs with radiation having a high energy level. Also, "b" represents a change in the image density of bones due to a beam hardening phenomenon, which occurs with radiation having a low energy level. With the method for forming a radiation image in accordance with the present invention, an image signal logSA is obtained which represents a radiation image recorded with radiation having a high energy level. Also, logSB is obtained which represents a radiation image recorded with radiation having a low energy level. Thereafter, the image signal components of the image signals logSA and logSB are subtracted from each other which represent corresponding picture elements in the two radiation images. From the subtraction process, a difference signal Ssub representing a radiation image of only the bones is obtained, which is expressed as $$KA \cdot logSA - KB \cdot logSB + KC = Ssub$$

wherein KA and KB denote weight factors, and KC denotes a bias component for adjusting such that the image density represented by the difference signal Ssub may become approximately equal to a predetermined level. In such cases, the tube voltage of a radiation source is adjusted such that image density change a: image density change b=subtraction factor KA: subtraction factor KB Therefore, the change in the image density of bones in the radiation image, which has been recorded with radiation having a high energy level, and the change in the image density of bones in the radiation image, which has been recorded with radiation having a low energy level, the changes being shown in FIG. 1, can be canceled each other by the ordinary subtracting operation. Accordingly, a radiation image accurately representing the bones can be obtained.

A first embodiment of the method for forming a radiation image in accordance with the present invention will be described hereinbelow.

Figure 2:
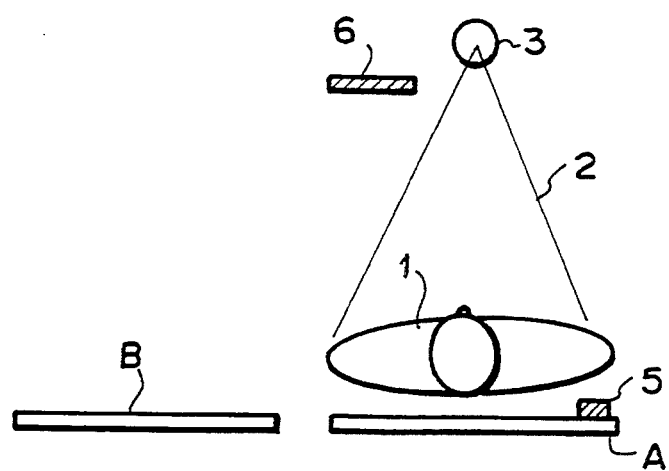
FIG. 2 is a side view showing how radiation images of an object are recorded in an embodiment of the method for forming a radiation image in accordance with the present invention.

With reference to FIG. 2, stimulable phosphor sheets A and B are sequentially exposed to X-rays 2, which have passed through an object 1 constituted of bones and soft tissues and which have different energy levels. Specifically, first, the tube voltage of an X-ray source 3 is set at 120 kV, and an X-ray image of the object 1 is stored on the stimulable phosphor sheet A with the X-rays 2 thus produced by the X-ray source 3. Thereafter, the stimulable phosphor sheet A is quickly removed from the position for exposure to the X-rays 2, and the stimulable phosphor sheet B is quickly set at the position for exposure to the X-rays 2. At the same time, an X-ray absorbing filter 6 (e.g. a 0.2 mm-thick copper filter), which can be inserted into and removed from the optical path of the X-rays 2, is located in the optical path of the X-rays 2. Also, the tube voltage of the X-ray source 3 is set at 46 kV. In this manner, an X-ray image of the object 1 is stored on the stimulable phosphor sheet B with the X-rays 2 having the different energy level. During the image recording operations, the positions of the stimulable phosphor sheets A and B with respect to the position of the object 1 are kept the same.

Figure 3:
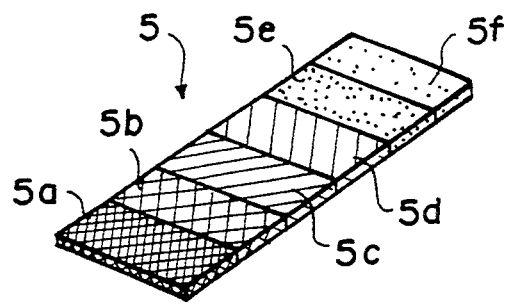
FIG. 3 is a perspective view showing an example of a bone calcium reference material used during the image recording step.

At this time, a bone calcium reference material (a phantom) 5, which is constituted of a plurality of sections the radiation absorption amounts of which are known and vary step-wise, is placed on each of the stimulable phosphor sheets A and B. In this manner, a pattern of the phantom 5 and the pattern of the object 1 are stored together on each of the stimulable phosphor sheets A and B. As shown in FIG. 3, the phantom 5 is constituted of sections 5a, 5b, 5c, 5d, 5e, and 5f, in which the content (wt %) of bone calcium, i.e. $CaCO_3$, varies step-wise. The contents of $CaCO_3$ in the sections 5a, 5b, 5c, 5d, 5e, and 5f are already known.

In this embodiment, the copper filter is employed as the X-ray absorbing filter 6. The material constituting the X-ray absorbing filter 6 is not limited to copper and may be selected from other materials. Also, the X-ray absorbing filter 6 may be constituted of a plurality of materials. The material constituting the X-ray absorbing filter 6 may be a mixture or a compound. Further, the X-ray absorbing filter 6 may be constituted of a plurality of filters placed one upon another.

In the manner described above, two X-ray images are stored on the stimulable phosphor sheets A and B. Thereafter, in an image read-out means shown in FIG. 4, the X-ray images are read out from the stimulable phosphor sheets A and B, and digital image signals representing the X-ray images are thereby obtained. Specifically, first, the stimulable phosphor sheet A is moved in the sub-scanning direction indicated by the arrow Y. At the same time, a laser beam 11, which serves as stimulating rays, is produced by a laser beam source 10. The laser beam 11 is deflected by a scanning mirror 12 and caused to scan the stimulable phosphor sheet A in the main scanning directions indicated by the double-headed arrow X. When the stimulable phosphor sheet A is exposed to the laser beam 11, it emits light 13 in proportion to the amount of energy stored thereon during its exposure to the X-rays 2. The emitted light 13 enters a light guide member 14, which is made from a transparent acrylic plate, from its one end face. The emitted light 13 is guided through repeated total reflection inside of the light guide member 14 and detected by a photomultiplier 15. The photomultiplier 15 generates an image signal S corresponding to the amount of the emitted light 13, i.e. representing the X-ray image stored on the stimulable phosphor sheet A.

The image signal S is converted into a digital image signal logSA having logarithmic values (logS) by a logarithmic converter 16 provided with an amplifier and an A/D converter. The digital image signal logSA is stored on a storage medium 17, such as a magnetic disk. Thereafter, the X-ray image stored on the stimulable phosphor sheet B is read out in the same manner as that described above. The digital image signal logSB representing the X-ray image stored on the stimulable phosphor sheet B is stored on the storage medium 17.

Figure 5:
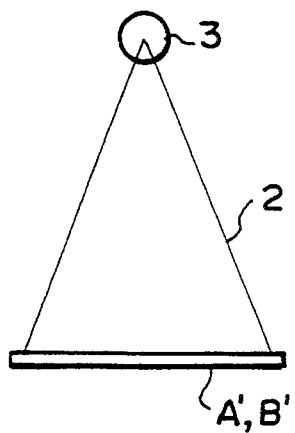
FIG. 5 is a side view showing a recording step for investigating nonuniformity in how radiation is irradiated to a stimulable phosphor sheet.
Figure 6A:
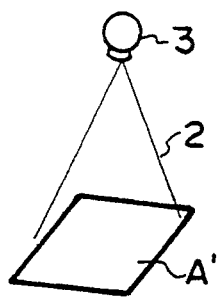
FIGS. 6A, 6B, 6C, and 6D are perspective views showing the recording steps in the embodiment of the method for forming a radiation image in accordance with the present invention.
Figure 6B:
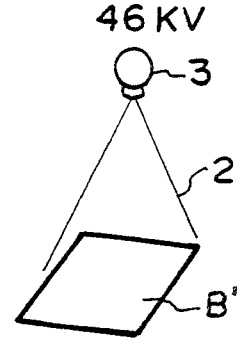
Figure 6C:
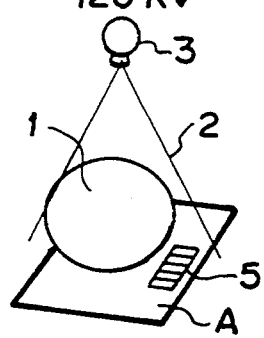
Figure 6D:
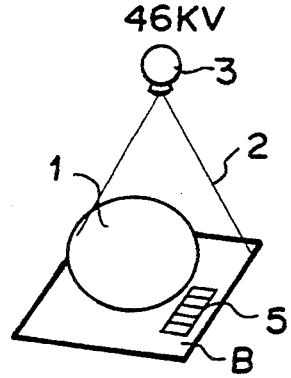
Figure 6E:
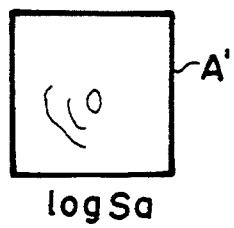
FIGS. 6E, 6F, 6G, and 6H are plan views showing examples of radiation images, which have been recorded with the recording steps of FIGS. 6A through 6D.
Figure 6F:
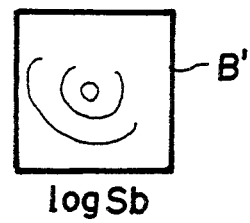
Figure 6G:
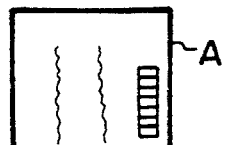
Figure 6H:
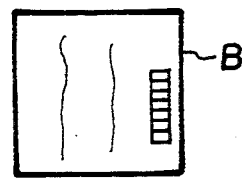

As described above, the X-ray images of the object 1 are sequentially stored on the stimulable phosphor sheets A and B by changing the tube voltage of the X-ray source 3 as shown in FIG. 2. Also, as shown in FIG. 5, stimulable phosphor sheets A' and B' are sequentially exposed to the X-rays 2, which are produced by changing the tube voltage of the X-ray source 3 in the same manner as that when the X-ray images of the object 1 were recorded as shown in FIG. 2. At this time, no object is placed between the X-ray source 3 and each stimulable phosphor sheet. In this manner, in order for nonuniformity in how the X-rays 2 are irradiated to the stimulable phosphor sheets A' and B' to be investigated, energy from the X-rays 2, which are produced by changing the tube voltage of the X-ray source 3, is stored on the stimulable phosphor sheets A' and B'.

Figure 4:
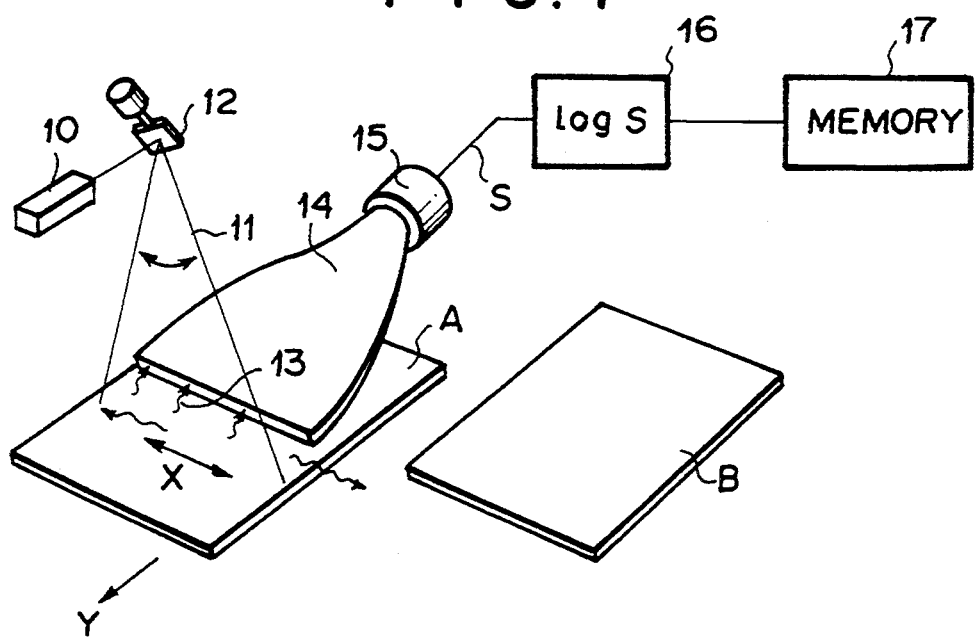
FIG. 4 is a perspective view showing how a radiation image is read out from a stimulable phosphor sheet in the embodiment of the method for forming a radiation image in accordance with the present invention.

Images stored on the stimulable phosphor sheets A' and B' are read out by the image read-out means shown in FIG. 4, and digital image signals are thereby obtained which represent nonuniformity in how the X-rays 2 are irradiated to the stimulable phosphor sheets A' and B'.

The recording steps described above are shown in FIGS. 6A, 6B, 6C, and 6D, and the X-ray images recorded with the recording steps are shown in FIGS. E, 6F, 6G, and 6H.

As shown in FIGS. 6A through 6H, a digital image signal logSa represents the X-ray image, which indicates the nonuniformity in how the X-rays 2 produced at a high tube voltage (120 kV) are irradiated to the stimulable phosphor sheet A' without an object intervening between the X-ray source 3 and the stimulable phosphor sheet A'. A digital image signal logSb represents the X-ray image, which indicates the nonuniformity in how the X-rays 2 produced at a low tube voltage (46 kV) are irradiated to the stimulable phosphor sheet B' without an object intervening between the X-ray source 3 and the stimulable phosphor sheet B'. A digital image signal logSA represents the X-ray image of the object 1 and the phantom 5, which image has been stored on the stimulable phosphor sheet A at the high tube voltage. A digital image signal logSB represents the X-ray image of the object 1 and the phantom 5, which image has been stored on the stimulable phosphor sheet B at the low tube voltage.

The digital image signals logSa and logSb, which represent the nonuniformity in how the X-rays 2 are irradiated to the stimulable phosphor sheets A' and B', are smoothed with a mask size of 1 cm×1 cm. In this manner, image signals logSa' and log Sb', which are now free of noise, are obtained and stored in the storage medium 17.

The digital image signal logSA and the X-ray irradiation nonuniformity signal logSa' are then subtracted from each other, and a digital image signal logSA' (=logSA−logSa') is thereby obtained which has been compensated for nonuniformity in how the X-rays 2 produced at the high tube voltage are irradiated to the stimulable phosphor sheet. Also, the digital image signal logSB and the X-ray irradiation nonuniformity signal logSb' are subtracted from each other, and a digital image signal logSB' (=logSB−logSb') is thereby obtained which has been compensated for nonuniformity in how the X-rays 2 produced at the low tube voltage are irradiated to the stimulable phosphor sheet.

Thereafter, a subtraction process is carried out on the digital image signals logSA' and logSB' which have been obtained in the manner described above. FIG. 7 is a block diagram showing how energy subtraction processing is carried out in the embodiment of the method for forming a radiation image in accordance with the present invention. First, the digital image signal logSa, which represents nonuniformity in how the X-rays having a high energy level are irradiated to the stimulable phosphor sheet, is read from an image file 17A in the storage medium 17. Also, the digital image signal logSA representing the X-ray image recorded with the X-rays 2 having a high energy level is read from an image file 17C. The digital image signals logSa and logSA are fed into an X-ray irradiation nonuniformity compensating circuit 18A. At this time, the image signal logSa' is obtained by eliminating noise from the image signal logSa, and a calculation is then made with the formula logSA−logSa'. In this manner, a digital image signal logSA' is obtained. Thereafter, the digital image signal logSb, which represents nonuniformity in how the X-rays having a low energy level are irradiated to the stimulable phosphor sheet, is read from an image file 17B in the storage medium 17. Also, the digital image signal logSB representing the X-ray image recorded with the X-rays 2 having a low energy level is read from an image file 17D. The digital image signals logSb and logSB are fed into an X-ray irradiation nonuniformity compensating circuit 18B. At this time, the image signal logSb' is obtained by eliminating noise from the image signal logSb, and a calculation is then made with the formula logSB−logSb'. In this manner, a digital image signal logSB' is obtained.

The digital image signals logSA' and logSB', which have been obtained in the manner described above, are fed into a subtraction operating circuit 19. The subtraction operating circuit 19 appropriately weights the digital image signals logSA' and logSB'. Thereafter, the subtraction operating circuit 19 subtracts the image signal components of the digital image signals logSA' and logSB' from each other which represent corresponding picture elements in the two X-ray images. From the subtraction process, a digital difference signal is obtained, which is expressed as $$S_{sub} = KA \cdot logSA' - KB \cdot logSB' + KC$$

wherein KA and KB denote weight factors, and KC denotes a bias component for adjusting such that the image density represented by the difference signal Ssub may become approximately equal to a predetermined level. The difference signal Ssub is stored in an image file 20 and is then fed into a display device 21, which reproduces and displays a subtraction image S. In the displayed subtraction image S, the change in the image density of bones in the X-ray image, which has been recorded with the X-rays having a high energy level, and the change in the image density of bones in the X-ray image, which has been recorded with the X-rays having a low energy level, the changes being shown in FIG. 1, have been canceled each other. Therefore, the subtraction image S accurately represents the image density of the bones.

The subtraction image S thus displayed is composed of a pattern S1 of a bone of the object 1 and a pattern S5 of the phantom 5. Therefore, the pattern S1 of the bone of the object 1 and the pattern S5 of the phantom 5 can be observed simultaneously. One of the step-like sections in the pattern S5 of the phantom 5 is found, which has an image density equal or close to the image density of a specific part of the pattern S1 of the bone, which part is to be analyzed for the determination of the amount of bone calcium. Thereafter, the amount of bone calcium can be determined which corresponds to the image density.

Figure 8:
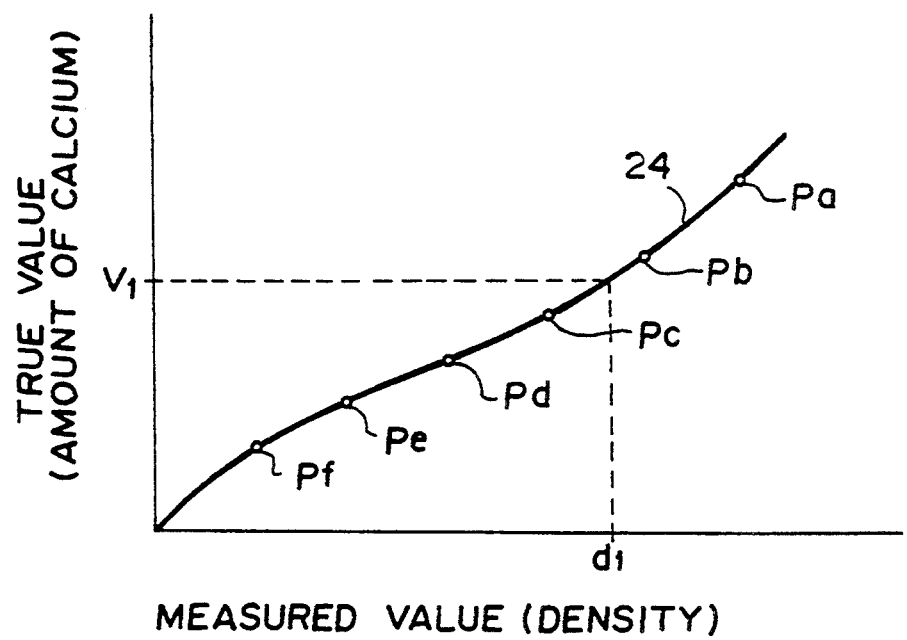
FIG. 8 is a graph showing an example of a calibration curve, which indicates the relationship between the measured value (the image density) and the true value (the amount of bone calcium) and which is used in an embodiment of the method for quantitatively analyzing bone calcium in accordance with the present invention.

For this purpose, as shown in FIG. 8, a calibration curve 24 is prepared which indicates the relationship between the amounts of $CaCO_3$ in the sections 5a, 5b, 5c, 5d, 5e, and 5f of the phantom 5 and the image densities of these sections in the subtraction image S1. From the calibration curve 24, the true value (the amount of bone calcium) can be found which corresponds to the measured value (the image density). For example, in cases where the image density of the specific part of the pattern S1 of the bone in the subtraction image S1 is equal to an intermediate value d1 between the image densities Pb and Pc of two adjacent sections in the pattern S5 of the phantom 5, the true value V1 corresponding to the image density d1 on the calibration curve 24 is determined as the amount of bone calcium.

The amount of bone calcium, which has been determined in the manner described above, may be displayed or recorded by one of various known display devices or recording apparatuses. For this purpose, information representing the amount of bone calcium found from the calibration curve 24 may be entered manually into the display device or the recording apparatus. Alternatively, the information representing the calibration curve may be stored in a table memory, and a position in the bone image may be designated on the display device 21. The image density at the designated position may then be converted into the amount of bone calcium in accordance with the calibration curve, and may thus be automatically displayed or recorded.

In such cases, in the pattern S1 of the bone, the change in the image density of bones in the X-ray image, which has been recorded with the X-rays having a high energy level, and the change in the image density of bones in the X-ray image, which has been recorded with the X-rays having a low energy level, the changes being shown in FIG. 1, have been canceled each other. Therefore, the pattern S1 of the bone accurately represents the image density of the bone.

In this embodiment, adverse effects of the shading (which occurs due to nonuniformity in how radiation is irradiated to each stimulable phosphor sheet during the image recording operation and nonuniformity in how the light emitted by each stimulable phosphor sheet is detected) should preferably be compensated for as in a method for quantitatively analyzing bone calcium proposed in Japanese Unexamined Patent Publication No. 5(1993)-111480.

A second embodiment of the method for forming a radiation image in accordance with the present invention will be described hereinbelow.

The second embodiment is identical with the first embodiment, except that the X-ray absorbing filter constituted of a 0.2 mm-thick copper filter is used also when the X-ray image is recorded with the X-rays having a high energy level.

Specifically, in the second embodiment, the X-ray absorbing filter is used both when the X-ray image is recorded with the X-rays having a high energy level and when the X-ray image is recorded with the X-rays having a low energy level. Therefore, the accuracy, with which the image density of the bone is expressed, becomes lower than in the first embodiment. However, with the second embodiment wherein the filter is kept in the optical path of the X-rays, the image recording operation can be carried out easily.

What is claimed is:

1. A method for forming a radiation image, comprising the steps of:
    irradiating an object comprising bone and soft tissue with first and second radiation having first and second energy levels, respectively, while exposing first and second stimulable phosphor sheets to said first and second radiation, respectively, to cause said first and second stimulable phosphor sheets to store first and second radiation images, respectively, of said bone and soft tissue of said object;
    exposing said first and second stimulable phosphor sheets to stimulating rays to cause said first and second stimulable phosphor sheets to emit first and second light, respectively, based on said first and second radiation images;
    detecting and converting said first and second light into first and second image signals, respectively; and
    subtracting said first and second image signals from each other to provide a difference signal representing an image of said bone of said object;
    said irradiating step comprising the step of:
        adjusting first and second tube voltages to be first and second optimum tube voltages which generate said first and second radiation having optimum energy levels so that when said first and second image signals are subtracted from each other in said subtracting step, a portion of said first image signal representing a change in density of said first radiation image of said bone occurring due to a beam hardening phenomenon of said first radiation and a portion of said second image signal representing a change in density of said second radiation image of said bone occurring due to a beam hardening phenomenon of said second radiation cancel each other.

2. A method for forming a radiation image as claimed in claim 1, wherein said first and second radiation are each X-rays.

3. A method for forming a radiation image as claimed in claim 1, wherein each of the stimulable phosphor sheets is two-dimensionally scanned with the stimulating rays.

4. A method for forming a radiation image as claimed in claim 1, wherein the stimulating rays are a laser beam.

5. A method as claimed in claim 1, wherein said first and second image signals are digital signals.

6. A method as claimed in claim 1, wherein said first energy level is higher than said second energy level.

7. A method for quantitatively analyzing bone calcium, comprising the steps of:
    irradiating an object comprising bone and soft tissue with first and second radiation having first and second energy levels, respectively, while exposing first and second stimulable phosphor sheets to said first and second radiation, respectively, to cause said first and second stimulable phosphor sheets to store first and second radiation images, respectively, of said bone and soft tissue of said object;

exposing said first and second stimulable phosphor sheets to stimulating rays to cause said first and second stimulable phosphor sheets to emit first and second light, respectively, based on said first and second radiation images;

detecting and converting said first and second light into first and second image signals, respectively;

subtracting said first and second image signals from each other to provide a difference signal representing an image of said bone of said object; and quantitatively analyzing calcium in said bone based on said difference signal;

said irradiating step comprising the step of:
adjusting first and second tube voltages to be first and second optimum tube voltages which generate said first and second radiation having optimum energy levels so that when said first and second image signals are subtracted from each other in said subtracting step, a portion of said first image signal representing a change in density of said first radiation image of said bone occurring due to a beam hardening phenomenon of said first radiation and a portion of said second image signal representing a change in density of said second radiation image of said bone occurring due to a beam hardening phenomenon of said second radiation cancel each other.

8. A method for quantitatively analyzing bone calcium as claimed in claim 7, wherein said first and second radiation are each X-rays.

9. A method for quantitatively analyzing bone calcium as claimed in claim 7, wherein each of the stimulable phosphor sheets is two-dimensionally scanned with the stimulating rays.

10. A method for quantitatively analyzing bone calcium as claimed in claim 7, wherein the stimulating rays are a laser beam.

11. A method as claimed in claim 7, wherein:
said irradiating step irradiates a pattern of bone calcium reference material with said first and second radiation, respectively, while exposing first and second stimulable phosphor sheets to said first and second radiation, respectively, to cause each of said first and second radiation images to include a radiation image of said bone calcium reference material;
said difference signal includes a first portion representing an image of said bone of said object and a second portion representing an image of said bone calcium reference material; and
said quantitatively analyzing step comprises the steps of:
generating said image of said bone of said object represented by said first portion of said difference signal and said image of said bone calcium reference material represented by said second portion of said difference signal; and
comparing said generated image of said bone of said object and said generated image of said bone calcium reference material with each other.

12. A method as claimed in claim 7, wherein said first and second image signals are digital signals.

13. A method as claimed in claim 7, wherein said first energy level is higher than said second energy level.

14. A method for quantitatively analyzing bone calcium, comprising the steps of:
irradiating first and second stimulable phosphor sheets with first and second radiation having first and second energy levels, respectively, to cause said first and second stimulable phosphor sheets to store first and second radiation energy, respectively;

exposing said first and second stimulable phosphor sheets to stimulating rays to cause said first and second stimulable phosphor sheets to emit first and second energy light, respectively, based on said first and second radiation energy;

detecting and converting said first and second energy light into first and second energy signals, respectively;

irradiating an object comprising bone and soft tissue with said first and second radiation, respectively, while exposing said first and second stimulable phosphor sheets to said first and second radiation, respectively, to cause said first and second stimulable phosphor sheets to store first and second radiation images, respectively, of said bone and soft tissue of said object;

exposing said first and second stimulable phosphor sheets to stimulating rays to cause said first and second stimulable phosphor sheets to emit first and second light, respectively, based on said first and second radiation images;

detecting and converting said first and second light into first and second image signals, respectively;

subtracting said first energy signal and said first image signal from each other, and said second energy signal and said second image signal from each other, to provide first and second subtracted signals, respectively;

subtracting said first and second subtracted signals from each other to provide a difference signal representing an image of said bone of said object; and quantitatively analyzing calcium in said bone based on said difference signal;

said object irradiating step comprising the step of:
adjusting first and second tube voltages to be first and second optimum tube voltages which generate said first and second radiation having optimum energy levels so that when said first and second subtracted signals are subtracted from each other in said subtracted signals subtracting step, a portion of said first subtracted signal representing a change in density of said first radiation image of said bone occurring due to a beam hardening phenomenon of said first radiation and a portion of said second subtracted signal representing a change in density of said second radiation image of said bone occurring due to a beam hardening phenomenon of said second radiation cancel each other.

15. A method as claimed in claim 14, wherein said first and second image signals and said first and second energy signals are digital signals.

16. A method as claimed in claim 14, wherein said first energy level is higher than said second energy level.

* * * * *